United States Patent [19]
Wood et al.

[11] Patent Number: 5,701,155
[45] Date of Patent: Dec. 23, 1997

[54] PROCESSOR MODULE FOR VIDEO INSPECTION PROBE

[75] Inventors: Robert J. Wood, Syracuse; Michael J. Piloski, Skaneateles; Gregory E. Pasik, Auburn, all of N.Y.

[73] Assignee: Welch Allyn, Inc., Skaneateles Falls, N.Y.

[21] Appl. No.: 581,304

[22] Filed: Dec. 28, 1995

Related U.S. Application Data

[63] Continuation of Ser. No. 944,129, Sep. 11, 1992, abandoned.

[51] Int. Cl.$^6$ .............................. A61B 1/04; H04N 7/18
[52] U.S. Cl. .............................. 348/72; 348/75
[58] Field of Search .................. 358/98; 128/6; 348/65, 72, 75, 82, 84, 85; H04N 7/18

[56] References Cited

U.S. PATENT DOCUMENTS

| | | | |
|---|---|---|---|
| 4,539,586 | 9/1985 | Danna | 358/98 |
| 4,667,656 | 5/1987 | Yabe | 348/65 |
| 4,862,258 | 8/1989 | Kidawara et al. | 358/98 |
| 4,885,635 | 12/1989 | Kimura et al. | 358/98 |
| 4,888,639 | 12/1989 | Yabe et al. | 358/98 |
| 4,974,075 | 11/1990 | Nakajima | 358/98 |
| 5,140,319 | 8/1992 | Riordan | 348/85 |
| 5,402,165 | 3/1995 | Linville et al. | 348/85 |
| 5,441,043 | 8/1995 | Wood et al. | 348/75 |
| 5,614,943 | 3/1997 | Nakamura et al. | 348/72 |

FOREIGN PATENT DOCUMENTS

| | | | |
|---|---|---|---|
| 63-292119 | 11/1988 | Japan | G03B 15/02 |

Primary Examiner—Tommy P. Chin
Assistant Examiner—Bryan S. Tung
Attorney, Agent, or Firm—Harris Beach & Wilcox,LLP

[57] ABSTRACT

A plug-in module for a video probe has a housing which contains video processing circuitry to receive a video output from a miniature video imager and produces a video signal suitable to apply, without further processing, to a video monitor. The module plugs into a mating socket of a power and illumination unit. A fiber optic bundle extends into a sleeve protruding from a proximal face of the module, and is positioned at the focus of a small, high efficacy lamp assembly. The housing of the plug-in module environmentally seals the electronic circuitry.

16 Claims, 3 Drawing Sheets

PROCESSOR MODULE FOR VIDEO INSPECTION PROBE

This is a continuation of application Ser. No. 07/944,129 filed Sep. 11, 1992, now abandoned.

BACKGROUND OF THE INVENTION

This invention relates to inspection devices, such as a borescope or endoscope, of the type in which a miniature video camera is mounted at a distal viewing head of an elongated insertion tube. The invention is more particularly concerned with an improved plug-in connector module for coupling the probe to a light and power source, and which contains all the circuitry necessary to process the output of the miniature video camera and deliver a video signal suitable to be applied directly to a video monitor.

It is desirable for the probe system to be compact and to operate at low power consumption rates, for example, so that the unit can be compact and of light weight, and also so that the unit can be made battery powered and portable.

A video laparoscope with a light source based on small, low-power metal halide discharge lamp is described in copending patent application Ser. No. 07/780,762, filed Oct. 22, 1991, and having a common assignee. As described in that patent application, a laparoscope or other similar probe has a miniature video camera that incorporates a miniature electronic imager and a lens assembly which are disposed either at the distal tip or at a proximal end of a flexible or rigid insertion tube. For insertion tubes of about 5 mm larger, the camera can be distally mounted. For very slim insertion tubes, the camera can be proximally mounted, with a relay lens system being contained in the insertion tube. The insertion tube can be rigid or can have its tip portion articulatable. The small video camera can be incorporated in an add-on camera attachment for laparoscopes having a proximal viewing port.

Disposing the camera at the distal tip of the laparoscope insertion tube reduces the amount of focussing and relay lenses to be carried in the tube. This means less light is lost in the lens system, so the amount of optical fiber bundle needed for illumination, is reduced which also permits the insertion tube to be made smaller.

The insertion tube proximal end is coupled through a flexible cable or umbilical to a connector module that plugs into a socket in a processor unit. A video cable that extends through the insertion tube and umbilical has terminals in the connector module that supply the video signal from the miniature camera to electronic circuitry in the processor, which supplies a suitable signal to a full color or monochrome monitor. An image of a target area, such as a tissue within a patient's body cavity, can be viewed on the monitor.

Also within the processor is a high illuminance, but low-wattage light source in the form of one or more metal halide discharge lamps. These can preferably be of the type described in copending patent application Ser. Nos. 07/484,166, filed Feb. 23, 1990; 07/636,743, and 07/636,744, each filed Dec. 31, 1990, and which have an assignee in common herewith. The lamp typically operates at a power of about 20 watts dc, and has an efficacy of at least 35 lumens per watt. The light produced, which can be controlled by the selection of salts employed, the dosage of mercury, and mechanical structure of the lamps, has an emission spectrum in the visible band, with very little radiation produced in the infrared band. Also, the arc gap of this lamp is small, which produces a small spot of light when focused onto the fiber optic bundle used for illumination. The small spot size allows almost all the light energy to be directed into the proximal end of a very small fiber bundle. The smaller illumination bundle permits the insertion tube to be made much smaller than was previously possible while still delivering plenty of light to the target area. Also, because small optical fiber bundles can be used, the probe can incorporate redundant optical fiber bundles, which can each be associated with a respective light source. Moreover, because the lamp operates at low power (e.g. 20 watts), producing limited infrared radiation, and with virtually all the light being focused onto the fiber optic bundle, the light source can be made much more compact, and the lamp power supply can be much smaller. The light incident on the target consists substantially only of visible light, with very little radiant heat. This permits the operator to view and examine living tissues or other delicate target materials for extended intervals without danger of tissue damage or the ignition of surgical drapes.

OBJECTS AND SUMMARY OF THE INVENTION

It is an object of this invention to provide an improved inspection probe that avoids the problems of the prior art.

It is another object to provide a video probe which has a self-contained plug-in video module containing the electronics for operating and delivering a video signal based on an image signal from the miniature video imager in the insertion tube.

In accordance with an aspect of this invention, a laparoscope, endoscope, borescope, or other similar probe has a miniature video camera associated with the insertion tube. The camera incorporates a miniature electronic imager and a lens assembly. A fiber optic bundle carries light for illuminating the target and emits light from the distal end of the probe.

A plug-in module contains the required video processing electronics within a sealed housing. The electronics receives power from a connector mounted on the housing, sends to the camera suitable control and synchronizing signals, and receives and processes image signals that represent the image of the target. From the electronics contained in the module, a video signal is provided to output terminals on the connector. The video signal can be directly fed to a suitable video monitor to provide a picture display of the target as viewed by the miniature camera. The illumination fiber optic bundle can be one bundle, or can be bifurcated so that it can receive light from two separate light sources. The bundle extends proximally from the proximal face of the module, and is supported in a projecting metal sleeve which serves to locate the end of the fiber bundle at the focus of the associated light source.

The module is profiled, in cross section, so that it fits insertably into a suitably profiled socket on a power and light unit. There is a power supply that provides power for the video circuitry to a mating connector within the socket, so that power is supplied to the connector on the module and also brings off the video signal when the module is positioned in the socket.

The above and many other objects, features, and advantages of this invention will become apparent to those skilled in the art from the ensuing description of an exemplary embodiment of this invention, to be read in conjunction with the accompanying Drawing.

DETAILED DESCRIPTION OF THE PREFERRED EMBODIMENT

Figure 1:
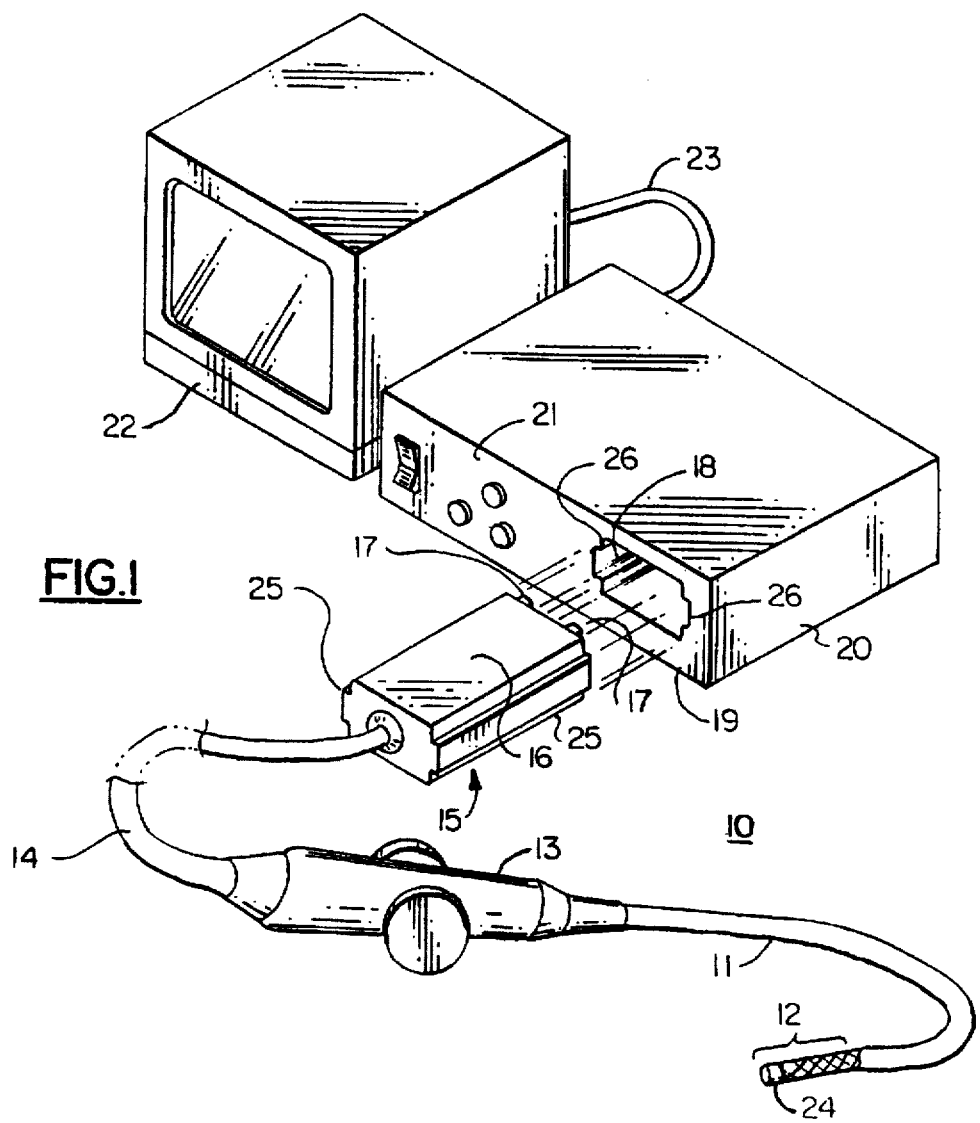
FIG. 1 is a perspective view of a probe assembly according to one of many possible embodiments of this invention.

With reference to the Drawing, and initially to FIG. 1, a borescope assembly 10 according to one embodiment of the present invention has an elongated, narrow insertion tube 11 having a distal tip 12 and a control handle 13 located at its proximal end. Wires, cables, and fiber optic bundles pass from the distal tip 12 through the insertion tube 11 and handle 13 and from there through a flexible tubular umbilical 14. The umbilical 14 is Joined by a strain relief to a sealed plug-in processing module 15. The module 15 has a sealed casing or housing 16 with protruding tubes or sleeves 17 that project from its proximal face. The processor module 15 serves as a connector module and plugs into a socket 18 on the front panel 19 of the cabinet of an associated light and power unit 20. The front panel 19 has associated controls and displays 21. A video monitor 22, which can be a color or black-and-white CRT, or can possibly be a projecting screen device or an LCD monitor, is coupled by a suitable cable 23 to the unit 20. The latter has a suitable wiring harness therein to connect the monitor 22 to the module 15. A miniature video camera 24 contains focusing lenses and a small solid-state imager, and is disposed in the distal tip 12 of the insertion tube 11.

Projecting ribs 25 on opposite side walls of the casing 16 serve as keys for fitting into mating recesses 26 in the sides of the socket 18. The ribs are positioned somewhat asymmetrically so that the module 15 cannot be inadvertently installed upside down.

Figure 2:
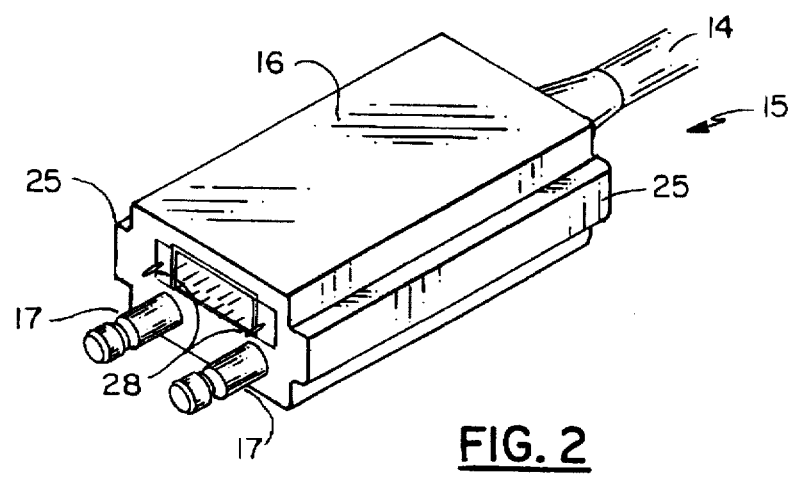
FIG. 2 is a perspective view of a video processor module according to this embodiment of the invention.

As shown in FIG. 2, there is a multi-pin electrical connector 27 disposed on the proximal wall of the module 15. This connector 27 includes several contact pins to bring power into the module and other pins which deliver a processed video signal that can be carried by the wiring harness and the cable 23 to the monitor 22. There are also a pair of locating pins or studs 28 disposed one on each side of the connector 27. These serve to locate or position the connector within the socket 18 when the processor module 15 is installed into the socket.

Figure 3:
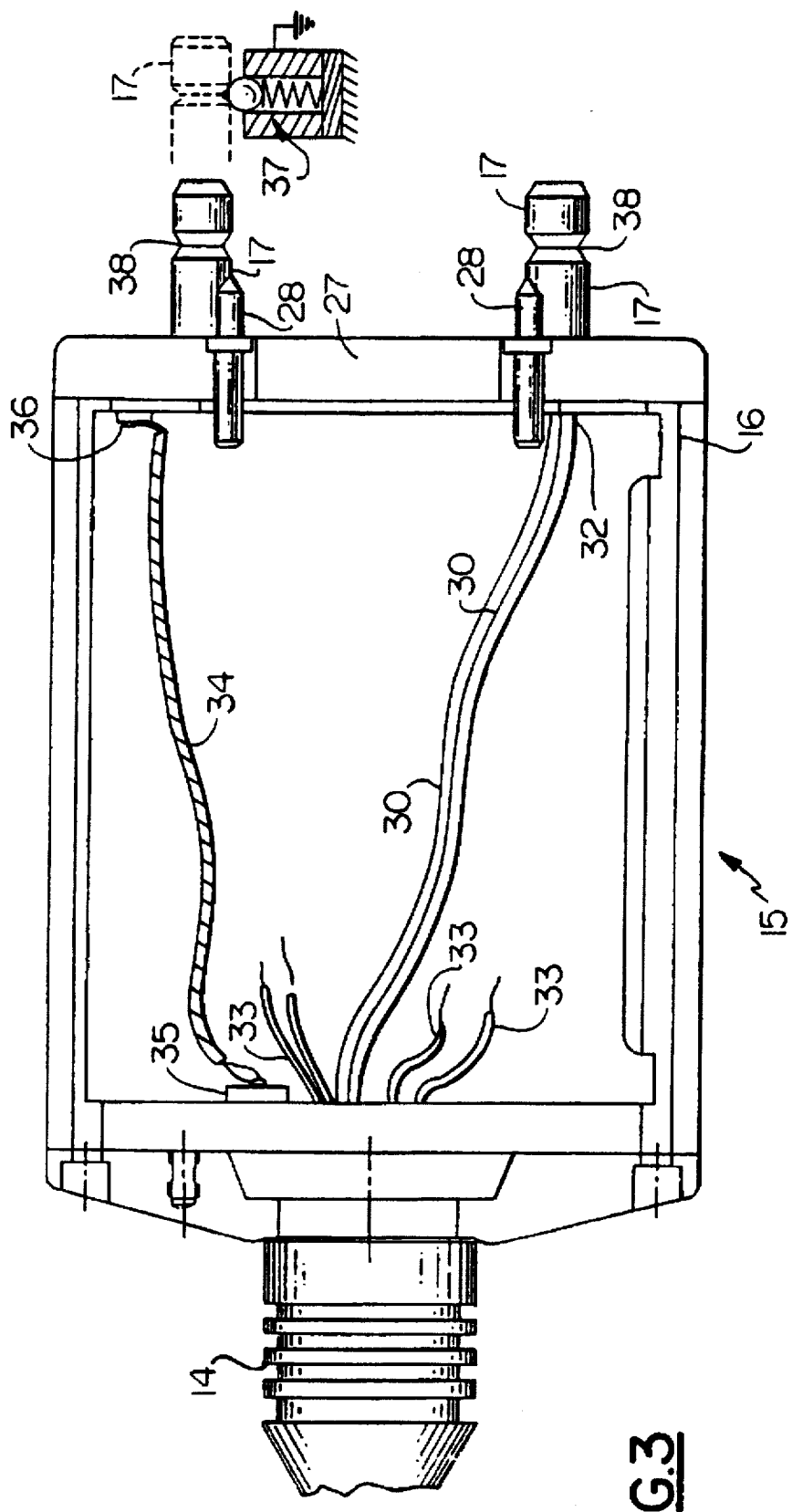
FIGS. 3 and 4 are top plan view of the video processor module showing progressive stages of assembly.

As shown in FIG. 3, in this case a fiber optic bundle 30 for carrying illumination to the distal end of the insertion tube 11 has a proximal end 32 disposed in one of the tubular sleeves 17. This sleeve 17 serves to position the proximal end 32 in position to receive light from a light source.

Also shown here are signal and control wires 33 which extend from the module 15, through the umbilical 14 and the insertion tube 11, to the camera 24. A grounding strap or pigtail 34 unites a ground conductor 35 in the umbilical to a grounding plate 36 disposed on the proximal side of the housing, and which is in electrical contact with each of the two sleeves 17.

Also shown here there is a retaining detent 37 within the unit 20 and which is electrically connected to chassis ground within the light and power unit 20. The detente 37 mechanically engages an annular recess 38 in the respective sleeve 17. This both couples the ground of the module 15 to the chassis ground of the unit 20, and also positions the fiber optic bundle end 32 accurately with respect to light sources to be described later.

Figure 4:
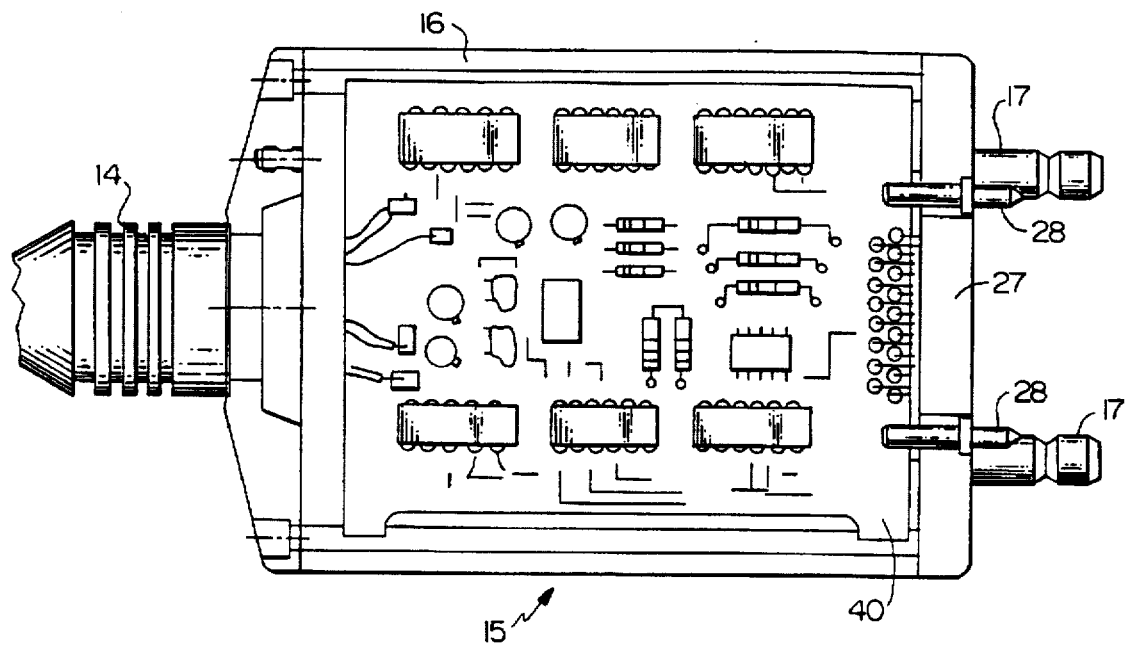

As shown in FIG. 4, one or more printed circuit boards 40 disposed within the module housing 16 contains electronics which derive power from certain ones of the contact pins of the connector 27, and the electronics also provide a processed video signal to other pins of this connector 27.

The video processing circuitry also provides synchronizing and control signals over the conductors 33 to the miniature camera 24. The circuitry on the board or boards 40 receives the image signal from the camera, and processes the same to produce a suitable video signal in a desired format, e.g. NTSC, PAL, etc, so that it can be applied directly to the video monitor 22. With this arrangement, each video camera 24 is matched with its own video circuitry contained within the module 15. This means that each probe unit is entirely modular, that is, completely interchangeable so that modular borescopes, endoscopes, or laparoscopes of different types can be employed using a single light and power unit 20. Also, any individual probe unit 10 can be used with any of various similar light and power units 20.

The probe unit 10 is entirely sealed, and can be completely immersed in ethylene oxide or another sterilization agent for sterilization between uses. The circuit board or boards 40 is environmentally sealed within the housing.

Figure 5:
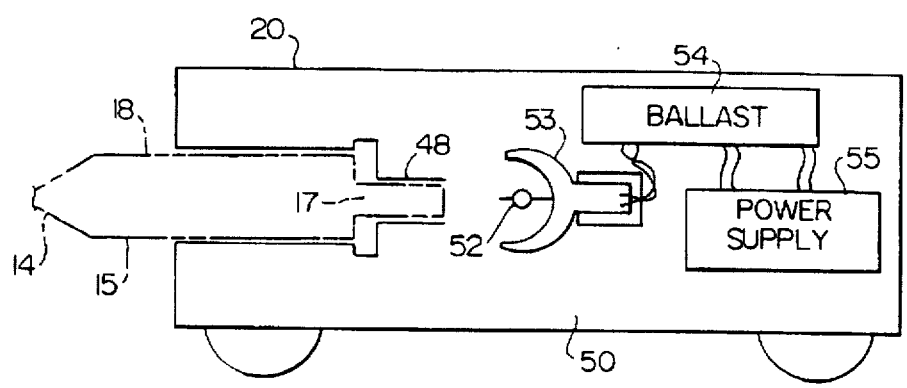
FIG. 5 is a schematic sectional view of a light and power unit of this invention.

As shown in FIG. 5, within the cabinet of the unit 20 and located behind the socket 18, there is a lamp assembly 50. This includes a low power metal halide discharge lamp 52 and an elliptical reflector 53, with the lamp 52 positioned at a first focus of the reflector. Positioned above the lamp and reflection is an associated ballast 54, i.e., a power supply for the lamp. Also within the cabinet is a power supply 55, which provides appropriate electrical current to the lamp ballast 54, and also provides the various required dc levels, through the coupler 27, to the electrical circuitry within the module 15.

The discharge lamp 52 is a low-wattage unit (e.g. 20 watts) containing suitable halide salts to emit white light, i.e. comprised of red, green and blue wavelengths, but without appreciable amounts of infrared radiation. The lamp has a very small arc gap so as to constitute a point source, whereby the reflected spot at its second focus is quite small.

Also within the socket 18 is a mating electrical connector (obscured in this view) which mates with the coupler 27 when the module 15 is completely inserted into the socket 18. Receptacles 48 are situated within the socket to receive and to locate the sleeves 17. These ensure that the fiber optic bundle end 32 is positioned at a location to receive the focussed spot of light from the lamp assembly 50.

While this invention has been described in detail with respect to a selected embodiment, it should be understood that the invention is not limited to that precise embodiment. Instead, many modifications and variations would present themselves to those of skill in the art without departing from the scope and spirit of this invention, as defined in the appended claims.

What is claimed is:

1. A video inspection probe by which a visual image of a remote target is reproduced on a video monitor of the type requiring a standard format video signal, and in which lens means focusses the image of the target onto a solid state imager which provides a video output for applying to said video monitor, comprising probe tube means carrying said lens means and said imager, and a processor module attached to a proximal end of said probe tube means including:

a module housing;

video processing circuit means contained within said housing and electrically coupled to said imager for processing said video output furnished by said imager and providing a standard format processed video output signal suitable to supply, without further processing, to said video monitor to reproduce said visual image thereon; and coupler means carried on said housing and having electrical power contacts to which power is delivered and applied to said video processing circuit means and output contacts for providing said standard format processed video output signal from said video processing circuit means to said monitor, wherein said module housing has a profile in cross section which is oblong with one or more protruding ribs for fitting into a mating recess of a power and illumination source, said mating recess having an oblong profile with one or more cutouts to receive said ribs.

2. A video inspection probe comprising:

a body;

a solid-state imager positioned within said body for viewing a target;

focussing means including at least one optical component for focussing an optical image of said target onto said imager; and an umbilical cable non-detachably connected at one end to said body, said cable having a processing module non-detachably connected at an opposite end, said module including a compact housing having video processing circuitry means retained therein for processing a signal of said target from said imager into a video monitor-ready video signal, said compact housing being detachably engageable with a combined light and power supply unit, said unit having receiving means including a cavity for accommodating said compact housing therein.

3. A video inspection probe as recited in claim 2, wherein said module housing includes coupler means for electrically interconnecting said light and power supply unit with said probe when said housing is attached thereto through said cavity and means for transmitting a processed video signal to a monitor attached to said light and power supply unit.

4. A video inspection probe as recited in claim 3, further including an illumination conduit extending from said combined light and power supply unit to said probe through said umbilical cable.

5. A video inspection probe as recited in claim 3, wherein said module housing is environmentally sealed.

6. A video inspection probe as recited in claim 2, wherein said probe is an endoscope.

7. A video inspection probe as recited in claim 2, wherein said probe is a borescope.

8. A video inspection probe as recited in claim 2, wherein said housing has a profile in cross section which is oblong with at least one protruding rib member for fitting into said cavity, said cavity having at least corresponding cutout for receiving said at least one rib member.

9. A video inspection system comprising video inspection probe including body;

solid-state imager positioned within said body for viewing a target;

focussing means including at least one optical component for focussing an optical image of said target onto said imager;

an umbilical cable non-detachably connected at one end to said body, said cable having a processing module non-detachably connected at an opposite end, said module including a compact housing having video processing circuitry means retained therein for processing a signal of said target from said imager into a video monitor-ready video signal;

a combined light and power supply unit having receiving means including a socket sized for accommodating said compact housing therein; and a video monitor for displaying a video signal processed by said processing circuitry means.

10. A video inspection system as recited in claim 9, wherein said housing has a profile in cross section which is oblong with at least one protruding rib member for fitting into said cavity, said cavity having at least corresponding cutout for receiving said at least one rib member.

11. A video inspection system as recited in claim 9 wherein said module housing includes coupler means for electrically interconnecting said light and power supply unit with said probe when said housing is attached thereto through said cavity and means for transmitting a processed video signal to said monitor attached to said light and power supply unit.

12. A video inspection system as recited in claim 9 further including an illumination conduit extending from said combined light and power supply unit to said probe through said umbilical cable.

13. A video inspection system as recited in claim 9 wherein said probe is an endoscope.

14. A video inspection system as recited in claim 9 wherein said probe is a borescope.

15. A video inspection system as recited in claim 9 wherein said module housing is environmentally sealed.

16. A video inspection system as recited in claim 9, including at least two video inspection probes, each said inspection probe having different video processing circuitry means retained in a processing module housing, each said housing being sized to interchangeably fit within said cavity of said combined light and power supply unit.

* * * * *